United States Patent [19]

Gementi et al.

[11] Patent Number: 4,956,484
[45] Date of Patent: Sep. 11, 1990

[54] PROCESS FOR PRODUCING A SILANE OR SILOXANE COMPOUND CONTAINING A CYCLOALKYL RING

[75] Inventors: Francesco Gementi, Milan; Loris Sogli, Novara; Raffaele Ungarelli, Trecate, all of Italy

[73] Assignee: Instituto Guido Donegani S.p.A., Novara, Italy

[21] Appl. No.: 163,948

[22] Filed: Mar. 3, 1988

[30] Foreign Application Priority Data

Mar. 6, 1987 [IT] Italy .................... 41003 A/87

[51] Int. Cl.$^5$ .................... C07F 7/08; C07F 7/10; C07F 7/18
[52] U.S. Cl. .................... 556/410; 556/413; 556/420; 556/423; 556/426; 556/427; 556/436; 556/437; 556/445; 556/446; 556/466; 556/482
[58] Field of Search ............... 556/410, 413, 420, 423, 556/426, 427, 436, 437, 445, 446, 482, 466

[56] References Cited

PUBLICATIONS

Selin et al., *Journal of American Chemical Society*, vol. 84, May 20, 1962, pp. 1856–1868.
Pitt et al., *Journal of Organometallic Chemistry*, vol. 121, 1976, pp. 37–43.
House, "Modern Synthetic Reacti0ns", 2nd Ed., W. A. Benjamin, Dec., Menlo Park, CA (1972), pp. 6–10.
Morrison and Boyd, "Organic Chemistry", 3rd Ed., Allyn & Bacon, Inc., Boston, (1980), p. 286.

*Primary Examiner*—Paul F. Shaver
*Attorney, Agent, or Firm*—Bryan, Cave, McPheeters & McRoberts

[57] ABSTRACT

A process for producing a silane or siloxane compound containing at least one cycloalkyl ring by hydrogenation of a corresponding derivative containing at least one aromatic ring in the presence of a Raney nickel catalyst modified with chromium.

14 Claims, No Drawings

PROCESS FOR PRODUCING A SILANE OR SILOXANE COMPOUND CONTAINING A CYCLOALKYL RING

BACKGROUND OF THE INVENTION

1. Field of the Invention

The present invention relates to a process for producing a silane or siloxane compound containing at least one cycloalkyl ring by catalytic hydrogenation of a corresponding derivative containing at least one aromatic or heteroaromatic ring.

2. Description of Related Art

The catalytic hydrogenation of tolyl-triethoxysilane having the formula II:

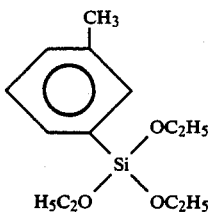

has been described in the Journal of American Chemical Society, Vol. 84, May 20, 1962, pp. 1856–1868, the hydrogenation being carried out in the presence of a Raney nickel catalyst at temperatures ranging from 95° to 105° C. over 16 hours at a pressure of 1,000 p.s.i., resulting in a yield of 54%.

The foregoing process is not acceptable for industrial use because of the yield and productivity, as well as because of the high pressure necessary for carrying out the hydrogenation. The yield level is particularly poor using the operating conditions described in the above-mentioned publication in the case of hydrogenation of certain aryl alkoxy-silanes that would be highly useful from an industrial point of view. Moreover, it has been virtually impossible to avoid massive hydrogenolysis of the carbon-silicon bonds.

SUMMARY OF THE INVENTION

The invention relates to a process for producing a silane or siloxane containing at least one cycloalkyl ring by catalytic hydrogenation of a corresponding derivative containing at least one aromatic or heteroaromatic ring and having the formula (I):

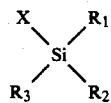

wherein:

X is an aryl, alkylaryl or arylalkyl group having from 6 to 20 carbon atoms, optionally containing, in the chain or in the ring, at least one hetero atom which may be oxygen, sulfur or nitrogen, and optionally, a halogen atom in the place of a hydrogen atom, or X may be the radical:

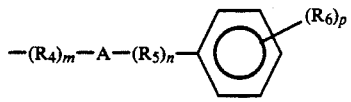

wherein $R_4$ or $R_5$ may be the same or different and are alkylene radicals containing from 1 to 20 carbon atoms; $R_6$ is an alkyl, alkoxy, alcoholic, acid, or ester radical containing from 1 to 20 carbon-atoms; A is a hetero atom as defined above; m, n and p may each be zero or a whole number from 1 to 10; and $R_1$, $R_2$ and $R_3$ are the same or different and may have the same meaning as X or may be hydrogen, an alkyl or alkylene radical containing from 1 to 20 carbon atoms, a linear or branched alkyl radical having from 1 to 20 carbon atoms and containing one or more alkoxy, carbonyl or carboxyl groups, or the group $N(R'')_2$ in which $R''$ is a hydrogen atom or an alkyl radical containing from 1 to 20 carbon atoms.

DESCRIPTION OF SPECIFIC EMBODIMENTS

Referring to the foregoing Summary of the Invention, we have now found that there is a particular kind of catalyst which results in excellent, unexpectedly high yields, not only for tolyl-triethoxysilane of the formula (II), but for silane or siloxane compounds of the formula (I), which until now either could not be hydrogenated, or could only be hydrogenated under burdensome operating conditions and would result in poor or even negligible yields, with considerable losses due to hydrogenolysis.

Therefore the invention, in its broadest aspect, relates to a process for producing a silane or siloxane containing at least one cycloalkyl ring by catalytic hydrogenation of a corresponding aryl derivative of formula (I), wherein the catalyst is a particular kind of Raney nickel modified with chromium.

The chromium content in the Raney nickel should be at least 0.1% by weight, and preferably is from about 1 to about 10%, and more preferably from about 2 to about 5% by weight, with reference to the nickel.

This type of nickel-chromium catlyst is described, for example, in U.S. Pat. Nos. 3,821,305 and 2,502,348, and it is known and sold commercially, for instance as "Raney 2400 Chromium promoted nickel" produced by the W. R. Grace Company, U.S.A.

According to the process of the present invention, the hydrogenation is carried out in the presence of an organic solvent, preferably an apolar solvent such as a saturated hydrocarbon, e.g., n-hexane or cyclohexane, with the amount of solvent generally ranging from about 0.1 to about 10 kg per kg of the compound that is to be hydrogenated.

The amount of catalyst to be used in the process of the present invention is not critical and can range from 50 to 500 kg per kg of the compound to be hydrogenated.

According to a preferred embodiment, the hydrogenation is carried out at temperatures ranging from about 50° C. to about 150° C., at a pressure ranging from about 5 to about 100 bar, preferably from about 10 to about 20 bar, and with a reaction time ranging from about 0.5 to about 50 hours, and preferably from about 1 to about 20 hours.

The advantages of the present invention are particularly apparent when one considers that the cycloalkyl derivatives of silanes and siloxanes previously obtained industrially have entailed a complicated process that used cyclohexene as the starting raw material. See, e.g., the Journal of Organometallic Chemistry, Vol. 121 (1976), at page 40 et seq.

Suitable silanes and siloxanes which can be obtained by the process of the present invention include the following:

(cyclohexyl)-Si—(OCH₃)₃; (cyclohexyl)₂-Si—(OCH₃)₂;

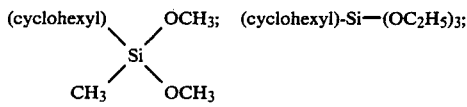

(cyclohexyl)₂-Si—(OC₂H₅)₂;

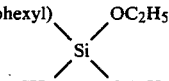

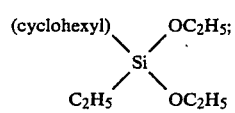

1,3-dicyclohexyl-tetramethyl-disiloxane;
tetracyclohexyl-oxysilane;
tetracyclohexyl-silane.

The silanes and siloxanes obtained by the process of the present invention may be advantageously used for preparing catalysts for the polymerization of olefins.

The folllowing examples are by way of illustration and not limitation.

EXAMPLES 1-4

An amount, as set forth in Table 1, of a Raney nickel-chromium catalyst, sold by Grace Company as "Raney 2400 chromium promoted nickel," containing 2-3% by weight of chromium, was loaded in the form of a suspension in a solvent at 30% by weight into an autoclave having a volume of 500 cm³. Then there was added methyl-phenyl-dimethoxysilane in the amount set forth in Table 1, together with an additional solvent until the total volume reached 200 cm³. The mixture was heated gradually over a period of one hour under strong stirring at the temperature and hydrogen pressure set forth in Table 1. After the reaction time indicated in Table 1, the hydrogenation was substantially complete. The final mass was cooled, the catalyst was separated by decantation and filtration, and the solvent was evaporated. Methyl-cyclohexyl-dimethoxy-silane was obtained, having a purity of 99.6%, in the amounts and yields set forth in Table 1.

TABLE 1

| Examples | 1 | 2 | 3 | 4 |
|---|---|---|---|---|
| Catalyst (g) | 34 | 23 | 23 | 48 |
| Methyl-phenyl-dimethoxy-silane (MPDS); (g) | 150 | 133 | 130 | 200 |
| Solvent | n-hexane | n-hexane | n-hexane | methano |
| T (°C.) | 90–95 | 90 | 90–95 | 94–107 |
| Pressure H₂ (bar) | 12–16 | 16 | 50 | 16–60 |
| Ratio Catalyst/MPDS (g/kg) | 227 | 174 | 173 | 240 |
| Ratio Solvent/MPDS (kg/kg) | 0.9 | 0.9 | 0.9 | 1.2 |
| Time (hours) | 4 | 6 | 3 | 19 |
| Methyl-cyclohexyl-dimethoxy-silane (g) | 132.3 | 131 | 107.4 | 154.3 |

TABLE 1-continued

| Examples | 1 | 2 | 3 | 4 |
|---|---|---|---|---|
| Yield | 85% | 95% | 80% | 75% |

EXAMPLES 5-6

Example 1 was repeated, however replacing the methyl-phenyl-dimethoxy-silane with diphenyl-dimethoxy silane. The operative conditions and the results obtained are set forth in Table 2.

TABLE 2

| Examples | 5 | 6 |
|---|---|---|
| Catalyst (g) | 22 | 12 |
| Diphenyl-dimethoxy-silane (DMPS) (g) | 163 | 170 |
| Solvent | n-hexane | n-hexane |
| T (°C.) | 84–94 | 92–94 |
| Pressure H₂ (bar) | 10–20 | 16–20 |
| Ratio catalyst/DMPS (g/kg) | 137 | 68 |
| Ratio solvent/DMPS (kg/kg) | 0.8 | 0.8 |
| Time (hours) | 3 | 7 |
| Dicyclohexyl-dimethoxy-silane (g) | 166.6 | 171.2 |
| Yield | 95% | 93% |

Variations in the foregoing description may of course be made without departing from the spirit of our invention.

We claim:

1. A process for producing a silane or siloxane compound containing a cycloalkyl ring by catalytic hydrogenation, this process comprising hydrogenating, in the presence of a Raney nickel catalyst modified with chromium wherein the chromium content is from about 1 to 10% by weight of the nickel, a silane or siloxane compound containing at least an aromatic or heteroaromatic ring and having formula (I):

wherein X is an aryl, alkylaryl or arylalkyl group having from 6 to 20 carbon atoms or the radical

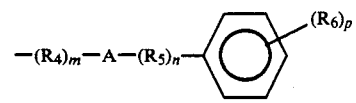

wherein $R_4$ and $R_5$ are the same or different and are each an alkylene radical containing from 1 to 20 carbon atoms; $R_6$ is an alkyl, alkoxy, alcohol, acid or ester radical containing from 1 to 20 carbon atoms; A is a heteroatom selected from the group consisting of oxygen, sulfur, nitrogen; m, n and p are zero or a whole number from 1 to 10; and $R_1$, $R_2$ and $R_3$ are the same or different and have the same definition as X or may be a hydrogen atom, an alkyl or alkylene radical containing from 1 to 20 carbon atoms, a linear or branched alkyl radical having from 1 to 20 carbon atoms and containing one or more alkoxy, carbonyl or carboxyl groups, or the group $N(R'')_2$ in which $R''$ is a hydrogen atom or an alkyl radical containing from 1 to 20 carbon atoms.

2. The process of claim 1 wherein X is the radical

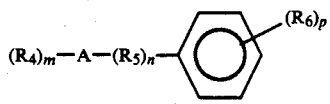

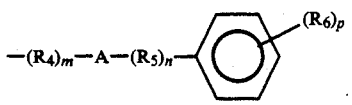

wherein $R_4$ and $R_5$ are the same or different and are each an alkylene radical containing from 1 to 20 carbon atoms; $R_6$ is an alkyl, alkoxy, alcohol, acid or ester radical containing from 1 to 20 carbon atoms; A is a heteroatom selected from the group consisting of oxygen, sulfur and nitrogen; and m, n and p are 0 or a whole number from 1 to 10.

3. The process of claim 1, wherein X contains at least one halogen atom in place of a hydrogen atom.

4. The process of claim 1, wherein the chromium content in the Raney nickel catalyst is at least 0.1% by weight of the nickel.

5. The process of claim 1, wherein the chromium content is from about 2 to 5% by weight of the nickel.

6. The process of claim 1, wherein the amount of the catalyst employed is from about 5 to 500 g per kg of said compound (I).

7. The process of claim 1, wherein the hydrogenation is carried out in the presence of an organic solvent, the solvent being present in an amount of from about 0.1 to about 10 kg per kg of said compound (I).

8. The process of claim 7, wherein said solvent is apolar.

9. The process of claim 8, wherein the solvent is n-hexane or cyclohexane.

10. The process of claim 1, wherein the hydrogenation is carried out at a temperature of from about 50° C. to 150° C.

11. The process of claim 1, wherein the hydrogenation is carried out at a hydrogen pressure of from about 5 to 100 bar.

12. The process of claim 10, wherein the hydrogen pressure is from about 10 to about 20 bar.

13. The process of claim 1, wherein the reaction time is from about 0.5 to about 50 hours.

14. The process of claim 13, wherein the reaction time is from 1 to 20 hours.

* * * * *

UNITED STATES PATENT AND TRADEMARK OFFICE
CERTIFICATE OF CORRECTION

PATENT NO. : 4,956,484

DATED : September 11, 1988

INVENTOR(S) : FRANCESCO GEMENTI et al.

It is certified that error appears in the above-identified patent and that said Letters Patent is hereby corrected as shown below:

Column 2, line 11: Delete "-"

Column 3, line 5: Change "et seg." to --et seq--.

Column 3, line 62: Change "methano" to --methanol--.

Column 4, line 45: Begin "X" is an aryl..." on a new line.

Signed and Sealed this

Fourteenth Day of July, 1992

Attest:

DOUGLAS B. COMER

Attesting Officer

Acting Commissioner of Patents and Trademarks